United States Patent [19]

MacLeay

[11] Patent Number: 4,604,455

[45] Date of Patent: Aug. 5, 1986

[54] PROCESS OF PREPARING AZOALKANE MIXTURE CONTAINING AT LEAST ONE UNSYMMETRICAL AZOALKANE

[75] Inventor: Ronald E. MacLeay, Erie, N.Y.

[73] Assignee: Pennwalt Corporation, Philadelphia, Pa.

[21] Appl. No.: 681,731

[22] Filed: Dec. 14, 1984

[51] Int. Cl.$^4$ ............................................ C07C 107/02
[52] U.S. Cl. ..................................... 534/587; 502/167; 525/25; 526/141; 528/274; 528/288; 534/573; 534/838; 534/886; 564/95
[58] Field of Search ............... 534/573, 587, 838, 886; 502/167; 525/25; 526/141; 528/288, 274

[56] References Cited

PUBLICATIONS

Engel et al., J. Am. Chem. Soc., vol. 97, pp. 6754 to 6762, (1975).
Ohme et al., Chemical Abstracts, vol. 63, 5515d, (1965).
Spialter et al., J. Org. Chem., vol. 30, pp. 3278 to 3283, (1965).

Primary Examiner—Floyd D. Higel

[57] ABSTRACT

Mixtures of azoalkanes of varying thermal stabilities at least one of which is an unsymmetrical azoalkane (R—N=N—R'), are prepared by reacting 4 equivalents of a mixture of two or more primary alkyl, cycloalkyl or aralkylamines with 1 equivalent of sulfuryl chloride in an inert solvent and oxidizing the resulting mixture of sulfamide products with basic bleach. The unsymmetrical azoalkanes can be separated from the symmetrical azoalkanes by a variety of conventional techniques. The azoalkane mixtures are excellent polymerization initiators for vinyl monomers and curing agents for unsaturated polyester resins.

8 Claims, No Drawings

PROCESS OF PREPARING AZOALKANE MIXTURE CONTAINING AT LEAST ONE UNSYMMETRICAL AZOALKANE

BACKGROUND OF THE DISCLOSURE

1. Field of the Invention

This invention relates to azoalkane mixtures containing unsymmetrical azoalkanes, a process for preparing such mixtures and the use of such mixtures in polymerizing vinyl monomers and curing unsaturated polyester resins.

2. The Problem

Various important properties of azoalkanes (R—N=N—R'), such as physical state, solubility, volatility, toxicity, thermal stability, and initiator efficiency, are dependent upon the nature of the alkyl groups R and R'. The thermal stability of the unsymmetrical azoalkanes (R≠R') is intermediate between the stabilities of the symmetrical azoalkanes R—N=N—R and R'—N=N—R' (P. S. Engel, Chemical Reviews, 80, pp. 101-109 (1980). Therefore, many of the unsymmetrical azoalkanes have unique thermal and initiator properties (depending upon R and R'), which cannot be duplicated by the symmetrical azoalkanes. These unique properties make them commercially desirable as free radical initiators. This is especially true when R and R' are tertiary groups.

Mixtures of an unsymmetrical azoalkane and the corresponding symmetrical azoalkanes have unique thermal and initiator properties that may extend over a wide temperature range depending upon the R and R' groups. For example, when tert-octylamine (1,1,3,3-tetramethylbutylamine) and tert-butylamine are used in the sulfamide reaction, a mixture of di-tert-octyldiazine (which has a ten hour half life (t-½) of 107° C.) and tert butyl tert-octyldiazene (which has a 10 hour half life of 137° C.) is obtained; the 10 hour half lives were extrapolated from data in J. W. Timberlake et al 1976 publication in the Journal of Organic Chemistry, vol 41, page 1666. Di-tert-butyldiazene (which has a 10 hour t-½ about 160° C. and a b.p. of 109° C.) is removed during the workup. Mixtures of tert-octylamine with tert-amylamine or tert-dodecylamine (Primene 81-R product) give mixtures of azoalkanes with similar half lives as above. Mixtures of initiators of various activities are commonly used in various polymerization processes. Mixtures of peroxides of different half lives are used in the polymerization of styrene, vinyl chloride, and ethylene. Mixtures of azonitriles are also used in polymerizations but these leave toxic residues in the polymers. Mixtures of azoalkanes derived from tert-octylamine and another tertiary alkyl primary amine are particularly useful where a low or intermediate temperature initiator is required to initiate the polymerization at a reasonable rate and a higher temperature initiator is required to finish the reaction. This is especially true in the bulk polymerization of styrene where a high temperature initiator is required to obtain faster conversion to polystyrene. Peroxides cannot be used in this capacity because they degrade polystyrene at the higher temperatures. Azonitriles are too unstable to be used as finishing catalysts. In fact, prior to our invention, no such suitable commercially feasible initiator system existed.

The ratio of the azoalkanes in the mixture and therefore the activity of the azoalkane mixture can be varied by varying the ratio of the amines used in the sulfamide reaction. The activity of the mixture can also be altered by adding one of the pure symmetrical diazenes to the mixture.

Prior to the present invention, mixtures of azoalkanes containing unsymmetrical azoalkanes were not commercially available due to the difficulty involved in preparing the unsymmetrical azoalkanes. Prior to the present invention, unsymmetrical azoalkanes were prepared by a variety of methods which were tedious, had many steps, and were not applicable to all classes of unsymmetrical azoalkanes.

3. Prior Art (A) Unsymmetrical Azoalkanes

P. S. Engle and D. J. Bishop prepared a series of unsymmetrical sulfamides by reacting methyl, isopropyl and tert-butyl sulfamyl chlorides with 2-amino-2-methyl-3-butene. The unsymmetrical sulfamides were oxidized to the corresponding unsaturated azoalkanes with basic bleach (P. S. Engel and D. J. Bishop, J. Am. Chem. Soc. 97, 6754 (1975). The sulfamyl chlorides are difficult to prepare and were made by the method of Weiss and Schulze (G. Weiss and G. Schulze, Justus Liebigs Ann. Chem., 729, 40, 1969). The method involves direct treatment of an amine hydrochloride with sulfuryl chloride either with or without a Lewis acid catalyst. The method is limited to simple alkyl amines and is often characterized by long reaction times, large excesses of reagents and low yields (J. A. Kloek and K. L. Leschinsky, J. Org. Chem. 41, 4028 (1976). Tert-Butyl sulfamyl chloride was especially difficult to prepare. Kloek and Leschinsky developed a better method of preparing sulfamyl chlorides but they still only got a 34% yield of tert-butyl sulfamyl chloride (J. A. Kloek and K. L. Leschinsky, J. Org. Chem., 41, 4028 (1976).

Treatment of tertiary alcohols with chlorosulfonyl isocyanate gives monoalkyl sulfamyl chlorides (J. B. Hendrickson and J. Joffe, J. Am Chem. Soc., 95, 4084, 1973). Timberlake used this method to synthesize N-tert-butyl-N'-tert-octylsulfamide in 44% yield (J. W. Timberlake, M. L. Hodges and A. W. Garner, Tetrahedron Lett., 3843, 1973 and J. W. Timberlake, J. Alender, A. W. Garner, M. L. Hodges, C. Ozmeral and S. Szilagyi, J. Org. Chem., 46, 20282, 1981). The sulfamide was oxidized with tert-butyl hypochlorite and sodim hydride to tert-butyl tert-octyldiazene. N-tert-Butyl-N'-(adamant-1-yl) sulfamide was prepared in 45% yield by the same route. There is no evidence it was oxidized to the azo. Apparently, tert-butyl tert-2,2,4,6,6-pentamethyl-4-heptyldiazene was also prepared by this route (J. W. Timberlake and A. W. Garner, J. Org. Chem., 41, 1666, 1976).

R. Ohme and H. Presuschhof tried preparing the unsymmetrical propyl butyldiazene by oxidizing a mixture of N,N'-di-propylsulfamide and N,N'-di-butylsulfamide. They only obtained 1,1'-azopropane and 1,1'-azobutane. None of the unsymmetrical azoalkane was formed (R. Ohme and H. Preuschhof, Liebigs Ann. Chem., 713, 74, 1968). This is the only example found in the literature of the direct preparation of a mixture of azoalkanes.

R. E. MacLeay and C. S. Sheppard (in U.S. Pat. No. 4,007,165) prepared unsymmetrical azoalkanes by reacting tert-alkyl-α-chloroazoalkanes with Grignard reagents and phenyl or alkyl lithium reagents. Although the unsymmetrical azoalkanes prepared by this route proved to be very good free radical initiators, the process proved to be commercially unattractive. Unsymmetrical tert-octyldiazenes were disclosed in this patent.

(B) Mixtures

Mixtures of azoalkanes of the structures R—N=N—R, R—N=N—R' and R'—N=N—R' and mixtures of R—N=N—R' and R'—N=N—R' were not found in the prior art.

(C) Process

The process of making mixtures of azoalkanes where at least one component of the mixture is an unsymmetrical azoalkane (R—N=N—R') was not found in the prior art.

Processes are known for the oxidation of N,N'-dialkylsulfamides to azoalkanes. Ohme and Preuschhof oxidized a mixture of N,N'-di-propylsulfamide and N,N'-di-n-butysulfamide to a mixture of 1,1'-azopropane and 1,1'-azobutane with basic bleach (R. Ohme and H. Preuschhof, Liebigs Ann. Chem., 713, 74, 1968). Ohme and Schmitz developed a general synthetic method for the preparation of low molecular weight azoalkanes (R. Ohme and E. Schmitz, Angew. Chem. Int. Ed. Engl., 4, 433, 1965). They found that the dialkylamides of sulfuric acid in a solution of alkali react with 2 moles of NaOCl at 20°–60° C. to form aliphatic azo compounds. They prepared azopropane, azobutane and azocyclohexane in this manner.

J. C. Stowell prepared 2,2'-azoisobutane in 84% yield by oxidizing N,N'-di-tert-butylsulfamide with basic bleach for 3 hours in pentane (J. C. Stowell, J. Org. Chem., 32, 2360, 1967). Ohme and Preuschhof oxidized the same sulfamide at 60° C. with basic bleach and also obtained an 84% yield of 2,2'-azoisobutane.

However, according to the prior art it is very difficult to oxidize many of the higher molecular weight N,N'-dialkylsulfamides with basic bleach. In 1972 J. W. Timberlake and co-workers attempted to prepare di-tert-octyldiazene and di-tert-heptyldiazene by this route but were unsuccessful (J. W. Timberlake, M. L. Hodges and K. Betterton, Synthesis 1972, 632–34). Treatment of either N,N'-bis(2,4,4-trimethyl-2-pentyl)sulfamide (i.e. N,N'-di-tert-octylsulfamide) or N,N'-bis-2,3,3-trimethyl-2-butyl)sulfamide (i.e. N,N;-di-tert-heptylsulfamide) under the conditions specified in Ohme's articles gave no azo compound. Timberlake recognized that the oxidation of sulfamides to azo compounds with basic bleach was not adaptable to all azos. The conditions were too vigorous for isolating unstable azo compounds and solubility problems in several cases led to quantitative return of starting sulfamides. Therefore, Timberlake developed a more complex method of converting N,N'di-tert-octylsulfamide into di-tert-octyldiazene using sodium hydride and tert-butyl hypochlorite (J. W. Timberlake, M. L. Hodges and K. Betterton, Synthesis, 1972, 632–34).

In 1978 a Japanese patent described a process for oxidizing N,N'-di-tert-octylsulfamide with bleach and caustic in the presence of a phase transfer catalyst (Japan Kokai 77,128,305; C. A., 88, 120602m, 1978). The reaction was run at 40° C. and required 10 hours to complete. This was the first indication that di-tert-octyldiazene could be prepared by the aqueous bleach route. The process required a phase transfer catalyst and a long reaction period.

In early 1982 a European Patent was published describing a photopolymerization process (R. Ohme and E. Schmitz, Angew. Chem. Int. Ed. Engl., 4, 433, 1965). In the patent, there is a description of the preparation of 2,2'-azobis(2,4,4-trimethylpentane) which is also referred to as di-tert-octyldiazene. The di-tert-octyldiazene was prepared by oxidizing N,N'-di-tert-octylsulfamide with bleach and caustic solution for 20 hours at 35° C. The yield was only 50% after purification by vacuum distillation.

In 1971 A. Ohno and co-workers reported the preparation of azobis(2-propyl)-2-propane by sodium hypochlorite oxidation of the corresponding sulfamide (A. Ohno, N. Kito and Y. Ohnishi, Bull. Chem. Soc. Japan, 1971, 44, 470–474). The azo was obtained in 38% yield after stirring 7.0 grams of the sulfamide in 50 mls of hexane with 150 mls of 10% NaOCl for 35 hours at room temperature.

SUMMARY OF THE INVENTION

The invention is directed to a mixture of azoalkanes of varying thermal stability where at least one component of the mixture is an unsymmetrical azoalkane having the structure R—R=N—R' and at least one component is a symmetrical azoalkane having the structure R—N=N—R or R'—N=N—R'.

This invention also relates to a simple process for preparing such a mixture from relatively inexpensive commercially available raw materials comprising reacting a mixture of two or more primary alkyl, cycloalkyl- or aralkylamines with sulfuryl chloride in an inert solvent and then oxidizing the mixture of sulfamide products with basic bleach after removing the amine hydrochloride side products with an aqueous wash. The amines used in the first step are employed in slight excess of a 4 to 1 molar ratio of amine to sulfuryl chloride.

It also relates to the use of the azoalkane mixtures as curing agents for unsaturated polyester resins or as polymerization initiators for vinyl monomers, especially in the bulk polymerization of styrene.

DETAILED DESCRIPTION OF THE INVENTION (A) Azoalkane Mixtures

The azoalkanes making up the mixture have the general structure R—N=N—R' and at least one of the azoalkanes in the mixture must be unsymmetrical, i.e., R≠R' where R and R' are independently selected from the following groups:
  (a) straight chain or branched alkyl of 1 to 22 carbons,
  (b) cycloalkyl of 3 to 12 carbons, and
  (c) aralkyl of 7 to 11 carbons,
with the proviso that R' can not be an aralkyl when R is an aralkyl and R' can not be identical to R for at least one of the azoalkanes.

The number of azoalkanes in the mixture can range from 2 to 100 but for practical purposes it is advisable to limit the number of azoalkanes in the mixture to about 2–15 and preferably from 2–10. Since the process of this invention generates a mixture of azoalkanes of varying thermal stabilities, it is advantageous to have the R and R' groups vary in structure. It is particularly advantageous if the R group contains β-branching such as the 1,1,3,3-tetramethylbutyl group (hereinafter referred to as the tert-octyl group) and the R' group is a tert- or sec-alkyl group without β branching. Such mixtures of azoalkanes can be generated from mixtures of tert-octylamine with tert-butylamine, tert-amyl-amine, cyclohexylamine, 2-ethylhexylamine or Rohm and Haas's Primene 81-R or Primene JM-T product [Primene 81-R is a trademark used to market a commercial mixture of isometric tert-alkyl primary amines in the $C_{12}$–$C_{14}$ range and Primene JM-T is a trademark used to market a commercial mixture of similar amines in the $C_{18}$–$C_{22}$ range].

(B) Process

The first step in the claimed process is carried out according to the method described in the accompanying U.S. patent application Ser. No. 681,729 of R. E. MacLeay, entitled "Process for the Preparation of Sulfamide Mixtures Containing Unsymmetrical N,N'-Disubstituted Sulfamides" filed concurrently herewith, and is herein incorporated by reference. Sulfuryl chloride is added to a solution of dried amines while controlling the temperature of the exothermic reaction below 20° C. The molar ratio of the amine mixture to the sulfuryl chloride is at least 4:1 and preferably slightly greater, i.e., about a 5% excess. Two moles of amine react with the sulfuryl chloride to form the sulfamide mixture and two moles of amine accept the hydrogen chloride generated, forming two moles of amine hydrochloride. The solution of the amines in the inert solvent must be absolutely dry to prevent side reactions and low yields. The amine hydrochlorides formed in the reaction are removed from the reaction mixture with an aqueous wash. The excess amine is removed with an acidic wash. Most amines can be recovered for recycle by treating the aqueous washes with excess caustic. Solvents suitable for the sulfamide step include hydrocarbon, chlorinated hydrocarbon, and ether solvents or mixtures thereof. If the sulfamide products are soluble in hydrocarbon solvents, it is advantageous to use a hydrocarbon solvent like hexane. If they are not soluble in hydrocarbon solvents, it is advantageous to use a chlorinated hydrocarbon solvent like methylene chloride. If they are partially soluble in hydrocarbon solvent, it may be advantageous to use a mixture of solvents like hexane and methylene chloride.

The amines suitable for the first step are the amines listed in U.S. patent application Ser. No. 681,729, "Process for the Preparation of Sulfamide Mixtures containing Unsymmetrical N,N'Disubstituted Sulfamides", filed concurrently herewith. The tert-alkyl primary amines are especially suitable for preparing azo initiators. A mixture of two primary aralkylamines were the aryl group is attached to the amino carbon, i.e., Ar—C—NH$_2$, is not preferred. Such a mixture would generate azoalkanes where both R and R' would contain aryl groups directly attached to the azo carbons and these azoaralkanes are too temperature sensitive in most cases to survive the preferred oxidation step temperature. However, when one of the amines is an $\alpha$-aralkylamine, such as tert-$\alpha$-cumylamine, the unsymmetrical azoalkane and one of the symmetrical azoalkanes are isolatable even though the symmetrical aralkylazoalkane (azocumene) decomposes under the preferred oxidation conditions.

The mixture of sulfamides obtained in the first step may be oxidized in the solvent they are isolated in, the solvent may be removed and another one added or the residue may be simply slurried in the basic bleach. Some sulfamides are more resistant to oxidation with basic bleach than others. In those cases the oxidation has to be run at higher temperatures and in a minimal amount of solvent. Generally the oxidation goes well at a temperature of 65°–90° C. in a minimal amount of solvent. Other sulfamides oxidize more readily and can be oxidized at lower temperatures in more dilute solutions. Phase transfer catalysts are advantageous but not necessary. They tend to speed up the rate of oxidation and minimize foaming during the reaction. In the oxidation of the more difficult to oxidize sulfamides, the solvent content can be reduced to a minimal amount prior to the addition of the oxidizing solution or during the oxidation reaction.

If two amines are used in the first step, the azoalkane mixture will contain an unsymmetrical azoalkane R—N=N—R' and generally two symmetrical azoalkanes. However, in some cases, one of the symmetical azoalkanes may be volatilized under the reaction conditions and may be removed during the oxidation. This is usually the case with di-tert-butyldiazene. The ratio of the azoalkanes in the mixture is dependent upon the ratio of the two amines used in the first step and the relative reactivity of the two amines. Optimization of the yield of the unsymmetrical azoalkane can be accomplished by varying the amine mole ratios in the sulfamide step.

If three amines are used in the first step, the azoalkane mixture will contain three unsymmetrical azoalkanes (R—N=N—R', R—N=N—R'' and R'—N=N—R'') and generally three symmetrical azoalkanes (R—N=N—R, R'—N=N—R' and R''—N=N—R''). However, in some cases one or two of the symmetrical azoalkanes may be lost during the oxidation if they are volatile. If more amines are used in the first step, the azoalkane mixtures will be more complex.

The unsymmetrical azoalkanes can be separated from the symmetrical azoalkanes by various methods such as recrystallization, gas, liquid, or column chromatography, preferential extraction into acid or vacuum distillation.

The oxidation requires at least two equivalents of sodium hypochlorite and one equivalent of sodium or potassium hydroxide per equivalent of sulfamide. However, it is advantageous to use excess bleach and caustic to speed up the reaction and insure complete oxidation since these raw materials are relatively inexpensive. Generally, a mole ratio of 2.5–2.8:1 of bleach to sulfamide and a mole ratio of 2.0–2.5:1 of caustic to sulfamide works well without being unduly wasteful. The excess bleach insures completion of reaction in a reasonable amount of time and the excess caustic stabilizes the bleach at the higher reaction temperatures. It is desirable to use 14–15% sodium hypochlorite in the oxidation. Normally higher concentrations of bleach are not commercially available. Weaker solutions of bleach work, but smaller batch sizes have to be run in a common reactor to accomodate the larger volume of water present. Sodium and potassium hydroxides are suitable bases for maintaining the high pH required.

In choosing the oxidation temperature, one should take into consideration the thermal stability of the azoalkanes produced. For instance, if di-tert-octyldiazene is one of the azoalkanes produced, the reaction temperature should be kept below 90° C. if possible to prevent thermal decomposition. If tert-amyl tert-cumyldiazene is the unsymmetrical azoalkane desired, the oxidation temperature should be held below 80° C. to avoid thermal decomposition. Normally temperatures of 65°–75° C. are adequate for oxidizing the sulfamide mixtures in a reasonable amount of time ($\frac{1}{2}$–3 hours). The oxidations can usually be monitored by gas chromatography or liquid chromatography and the reaction conditions can be adjusted to obtain complete oxidation in a reasonable amount of time and still prevent decomposition of the unsymmetrical azoalkanes as well as most of the symmetrical azoalkanes.

The oxidations may be run in the absence of solvent. However, normally it is advantageous to run the oxidation in the presence of at least a small amount of solvent. Hexane is the preferred solvent in most cases because its boiling point is approximately the reaction temperature desired (i.e., ~65° C.) and residual hexane can be readily removed from the product. If methylene chloride or a mixture of methylene chloride and hexane is used as the solvent for the sulfamide reaction, generally most of the methylene chloride has to be removed, either prior to the oxidation step or during the oxidation step. Otherwise, the reflux temperature of the system is too low to obtain oxidation of the sulfamides. In some cases the oxidation does not go if there is too much solvent present. In these cases the solvent level has to be reduced to a minimal amount either prior to the oxidation step or during the oxidation step.

Generally, the minimal amount of solvent is about 3 to 4 parts solvent to 1 part sulfamide. The solvent level in the reaction mixture can be reduced to the minimal level by equipping the reactor with a distilling head and condenser and distilling off the solvent until reaction occurs. It is usually obvious when reaction begins to occur when hexane is the solvent. The hexane begins to distill much faster and there is a rapid rise in reaction temperature of about 5°–10° C. The rate of heating can easily be adjusted to control the solvent distillation and the subsequent reaction.

Normally, small amounts of N-chloramines form in the oxidation step. Therefore, it is advisable to wash the crude azo with sodium bisulfite solution to reduce these bothersome impurities back to amines which go out in the acidic bisulfite solution. The solvents are normally removed by evaporative procedures under reduced pressure.

The azoalkane mixtures of this invention are initiators for the polymerization of vinyl monomers and curing agents for unsaturated polyester resins. The specific end uses of the azoalkane mixtures vary depending upon the thermal stabilities of the azoalkanes in the mixture and the relative amounts of each azoalkane in the mixture. The azoalkane mixture obtained from tert-cumylamine and tert-octylamine is useful in the polymerization of vinyl chloride and acrylic esters. The more stable azoalkane mixtures derived from tert-octylamine and tert-alkyl primary amines which do not contain β-branching are useful in the polymerization of styrene and para-methylstyrene. These mixtures are particularly useful in the bulk polymerization of styrene.

In general, polystyrene will have a molecular weight distribution $\overline{M}w/\overline{M}n$ in the range of 2 to 4 (usually 2.5–3), where $\overline{M}w$ is the weight average molecular weight and $\overline{M}n$ is the number average molecular weight (as determined by gel permeation chromatography). The usual commercial polystyrene processes are such that the polymerization time is of the order of about 8 to 14 hours, depending on the molecular weight. Usually, $\overline{M}w$ of commercial polystyrene is in the range of 200,000 to 350,000 and the molecular weight distribution is between 2 and 3.

Thermal polymerization is generally employed for the bulk polymerization of styrene. Attempts to speed up the polymerization by addition of peroxide initiators generally leads to lower molecular weight ($\overline{M}w$) and higher molecular weight distributions.

Over the past few years polystyrene producers have found that they can speed up their polymerizations and increase their capacity by adding small amounts of specific peroxide initiators to their bulk polymerization processes and gradually raising the polymerization temperature over a predetermined time period. The increase in capacity more than offsets the added costs of the initiators.

At present, the current commercial initiators are quickly consumed at the operating temperatures and there is no initiator (finishing catalyst) left to push the reaction to completion. Commercially there is a need for more stable free radical initiators that will survive longer and continue to initiate the polymerization during the later stages of the polymerization. In addition it is desirable that the initiator be non-volatile so that any residual initiator does not strip off with the residual monomer during the stripping step. In addition it is desirable that the high temperature initiator be an azoalkane so it does not degrade the polystyrene in the later stages of polymerization. It has been unexpectedly found that many of the azoalkane mixtures of the present invention fulfill this need.

Using one of the novel azoalkane mixtures of this invention in the solution polymerization of styrene resulted in molecular weight values similar to those of polystyrene produced under similar conditions without an initiator (thermal). The molecular weight distribution was unexpectedly narrower than the thermal polymer and 100% conversion of styrene to polystyrene was obtained compared to 92% conversion under thermal conditions. In contrast, polystyrene prepared using various peroxyketals as the initiators gave broader molecular weight distributions and only 92–97% conversion of styrene to polystyrene (See Example XXV infra). The narrow molecular weight distribution of the polystyrene obtained with the azoalkane mixture is a very desirable property.

For the bulk or solution polymerization of styrene, the preferred low temperature component of the azoalkane mixture is di-tert-octyldiazene which has a 10 hour t-½ of 107° C. The high or intermediate temperature components of the mixture are preferably unsymmetrical tert-octyldiazenes which have 10 hour t-½s in the range of 130°–145° C. Included in this group of azoalkanes are tert-octyl tert-dodecyldiazene, tert-octyl tert-tridecyldiazene, tert-octyl tert-tetradecyldiazene and tert-octyl cyclohexyldiazene. Among the acceptable high temperature initiators but less preferred due to their volatility are tert-butyl tert-octyldiazene, tert-amyl tert-octyldiazene and isopropyl tert-octyldiazene. Symmetrical azoalkanes having half life temperatures of 150°–170° C. also may contribute but are not necessary. This group of azoalkanes includes compounds such as di-cyclohexyldiazene, di-tert-tridecyldiazene, and di-tert-tetradecyldiazene.

The optimum amount of azoalkane mixture used in the polymerization will be dependent upon the polymerization technique used, the polymerization temperatures employed, the identity of the azoalkanes in the mixtures and the ratio of the low temperature azoalkane to the high temperature azoalkane(s). Too little initiator will result in low conversion of styrene to polystyrene under predetermined conditions and too much initiator is wasteful. Generally, the total weight of azoalkane mixture will be from about 0.001% to 1.0% by weight. For the bulk polymerization of styrene use of from about 0.01% to 0.5% by weight is employed and preferably from about 0.02% to 0.05%.

While the proportion of the high temperature sensitive initiator to low temperature sensitive initiator may vary considerably, it is advisable that the low temperature azoalkane be present in the major amount. The optimum proportion will be dependent upon the polymerization technique used and the polymerization temperatures employed.

The polymerization cycle must be adjusted for each azoalkane mixture to obtain the optimum results, i.e, the shortest time period required to obtain product of high molecular weight in high conversion. One skilled in the art can readily determine the optimum polymerization conditions by running a series of small scale polymerizations and comparing the results.

The polymerization temperature can be held constant or it can be raised gradually following a predetermined temperature cycle as disclosed in U.S. Pat. No. 4,125,695. The nature of the temperature cycle used influences the polymerization rate as well as the polymer's molecular weight. By using a programmed temperature cycle in the polymerization, one can use a substantial amount of the heat of polymerization to raise the temperature of the reaction mass and thus reduce the cooling capacity requirements of the commerical reactors.

When the polymerization is conducted in solution, the selection of the solvent used will be influenced by factors such as the solubility of the polymer, the chain transfer constant of the solvent, and the boiling point. Ethylbenzene is generally a very suitable solvent for the solution polymerization of styrene.

EXAMPLES

The examples demonstrate some of the various mixtures of azoalkanes that can be prepared by the method of this invention. They also demonstrate to a small degree how the percentages of the azoalkanes in the mixture change as the ratio of the amines in the sulfamide step change. The azoalkane mixtures were analyzed on a Hewlett Packard 5701A gas chromatograph coupled to a 3380S integrator using an 18 inch×$\frac{1}{8}$ inch 3% OV-17 column. Usually the temperature was programmed from 45° C. to 230° C. at 8° C. or 16° C./minute. When the Primene 81-R product and tert-octylamine were used as the amine mixture, the azoalkanes were analyzed by liquid chromatography.

When the Primene 81-R product is used with another amine, such as tert-octylamine, the azoalkane mixture is a mixture of 4 symmetrical and 6 unsymmetrical azoalkanes, i.e., $C_8$–$C_8$, $C_{12}$–$C_{12}$, $C_{13}$–$C_{13}$, $C_{14}$–$C_{14}$, $C_8$–$C_{12}$, $C_8$–$C_{13}$, $C_8$–$C_{14}$, $C_{12}$–$C_{13}$, $C_{12}$–$C_{14}$, and $C_{13}$–$C_{14}$. All these azoalkanes cannot be separated completely by gas or liquid chromatography. In Table I, the formula R—N=N—R' refers to a mixture of the three unsymmetrical diazenes, i.e., $C_8$–$C_{12}$, $C_8$–$C_{13}$ and $C_8$–$C_{14}$. All three or these azoalkanes have approximately the same thermal stability. Likewise, the formula R'—N=N—R' refers to a mixture of three symmetrical high molecular weight diazenes ($C_{12}$–$C_{12}$, $C_{13}$–$C_{13}$ and $C_{14}$–$C_{14}$) and three unsymmetrical high molecular weight diazenes ($C_{12}$–$C_{13}$, $C_{12}$–$C_{14}$, and $C_{13}$–$C_{14}$) and all six of these azoalkanes have approximately the same thermal stability which is greater than that of R—N=N—R'.

When tert-butylamine is used in the amine mixture, N,N'-di-tert-butylsulfamide is present in the sulfamide mixture. However, upon oxidation, di-tert-butyldiazene (being very volatile) is lost during the reaction, the workup, or the solvent stripping step (See Example II). The tert-butyl tert-octyldiazene is separated from the di-tert-octyldiazene by vacuum distillation. The pure tert-butyl tert-octyldiazene is distilled at 35° C. at 1.0 mm Hg.

General Procedure for the Preparation of Sulfamide Mixtures

Into a 1 liter 3-neck flask were added the appropriate amounts of the two amines and 200–300 ml of hexane. The flask was equipped with a magnetic stirrer, thermometer, and Dean Stark trap connected to a reflux condenser. The flask was then lowered into an 80° C. preheated oil bath and the hexane solution was refluxed using the Dean Stark trap to remove water which was azeotroped off with the hexane from the reaction mass for at least $\frac{1}{2}$ hours. The water that formed in the trap was separated and the hexane layer was added back to the reaction flask. The magnetic stirrer was then replaced with a mechanical stirrer and the flask was equipped with a 25 ml dropping funnel, air condenser, and thermometer. The hexane solution of the dried amines was cooled to 0° C. and the appropriate amount of 97% sulfuryl chloride was added dropwise from the dropping funnel over 20–30 minutes while holding the temperature below 15° C. After the addition was completed, the reaction was warmed to 30° C. and stirred $\frac{1}{2}$ hour at 25°–30° C. The reaction was diluted with water to dissolve the hydrochloride salts and was transferred to a separatory funnel. The aqueous layer was separated and the hexane solution was washed with 100 ml of dilute acid and 5% HCl or 10% $H_2SO_4$ to remove any residual amine. The acid layer was separated and added to the aqueous layer for amine recovery. The hexane solution of the sulfamides was either used as such in the oxidation step or stripped of hexane and then oxidized. The results of the individual examples are summarized in Table I.

General Procedures for the Oxidation of the Sulfamide Mixtures to Azoalkane Mixtures

Method A

The solution of the sulfamides was added to a 1 liter 3-neck round bottom flask along with 0.5 grams Adogen 464* (a trademark of Aldrich Chemical Company for its methyltrialkyl ($C_8$–$C_{10}$) ammonium chloride) phase transfer catalyst and a solution of 30–40 grams of 50% sodium hydroxide in 225–250 grams of 14.2% bleach (NaOCl). The flask was equipped with a magnetic stirrer, thermometer, and distilling head connected to a condenser and receiver. The flask was lowered into a preheated oil bath (~20° C.) and stirred vigorously with the magnetic stirrer. The reaction warmed up and most of the hexane distilled off. During the course of the distillation, oxidation occurred. There usually was a rapid exotherm toward the end of the distillation which lasted about 5 or 10 minutes and then slowly subsided. The reactions were stirred an additional $\frac{1}{2}$-1 hour after the exotherm subsided. At the end of the stir period, the reaction was cooled to 30° C. and the hexane that distilled off was added back to the reaction mixture. The aqueous bleach layer was separated and the hexane solution of the azoalkanes washed with 100 ml of water and then stirred $\frac{1}{2}$ hour with 100 ml of 15% sodium bisulfite solution to reduce any N-chloramines. After separation of the bisulfite solution, the hexane solution was washed successively with 100 ml portions of dilute acid, water, and saturated sodium bicarbonate solution. The hexane solution was dried over sodium sulfate, filtered, and the solvent was stripped off on a rotary evaporator under reduced pressure. The resultant azoalkane mixture was analyzed by gas or liquid chromatography. The results are summarized in Table I.

Method B

This oxidation method as similar to Method A except the sulfamide mixture was dissolved in about 100 mls of hexane and the hexane was not distilled off during the oxidation. Instead the hexane solution was refluxed during the oxidation step. When reaction began to occur, strong refluxing occurred in the condenser and the oil bath was usually lowered until the strong reflux died out. This usually lasted 5–10 minutes. Then the oil bath was raised again and the reaction refluxed gently for an additional hour. The remainder of the procedure and workup were the same as Method A. The results are summarized in Table I.

chromatographic scan of the hexane solution indicated the presence of six distinct peaks, the first of which was N,N'-di-tert-butylsulfamide.

The crude sulfamide mixture was dissolved in 80 mls of hexane and oxidized according to General Method B. The yellow liquid obtained after stripping off the hexane weighed 17.4 grams. Gas chromatographic analysis indicated that it consisted of 1.6% residual hexane, 10.6% of di-tert-amyldiazene, 6.4% tert-amyl-tert-butyldiazene, 37.4% tert-amyl tert-octyldiazene, 27.9% di-tert-octyldiazene and 16.1% tert-butyl tert-octyldiazene. There was no di-tert-butyldiazene present.

EXAMPLE XX

Preparation of a Mixture of Di-tert-Amyldiazene and tert-Amyl tert-Cumyldiazene tert-Cumylamine was prepared by saponifying tert-cumylurea with caustic in cellosolve. The crude amine

TABLE I

Examples I–XVIII

| Example | RNH$_2$ | Moles RNH$_2$ | R'NH$_2$ | Moles R'NH$_2$ | Moles SO$_2$CL$_2$ | MLS Hexane | Oxidn. Method | Azo Crude Yield | % Residual Hexane |
|---|---|---|---|---|---|---|---|---|---|
| I | t-C$_5$H$_{11}$NH$_2$ | 0.32 | t-C$_8$H$_{17}$NH$_2$ | 0.30 | 0.15 | 225 | B | 25.2 | 1.25 |
| II | t-C$_4$H$_9$NH$_2$ | 0.30 | t-C$_8$H$_{17}$NH$_2$ | 0.30 | 0.15 | 200 | A | 19.9 | 1.0 |
| III | t-C$_5$H$_{11}$NH$_2$ | 0.325 | Primene 81-R | ~0.30 | 0.15 | 300 | B | 27.0 | 9.3 |
| IV | t-C$_4$H$_9$NH$_2$ | 0.275 | Primene 81-R | ~0.35 | 0.15 | 300 | B | 25.0 | 1.9 |
| V | t-C$_4$H$_9$NH$_2$ | 0.325 | Primene 81-R | ~0.30 | 0.15 | 300 | B | 28.3 | 3.9 |
| VI | t-C$_4$H$_9$NH$_2$ | 0.50 | Primene 81-R | ~0.20 | 0.15 | 300 | B | 16.0 | 3.6 |
| VII | t-C$_8$H$_{17}$NH$_2$ | 0.20 | Primene 81-R | ~0.425 | 0.15 | 300 | B | 31.2 | 5.2 |
| VIII | t-C$_8$H$_{17}$NH$_2$ | 0.275 | Primene 81-R | ~0.35 | 0.15 | 300 | A | 31.5 | 1.9 |
| IX | t-C$_8$H$_{17}$NH$_2$ | 0.30 | Primene 81-R | ~0.325 | 0.15 | 300 | A | 32.1 | 2.6 |
| X | t-C$_8$H$_{17}$NH$_2$ | 0.325 | Primene 81-R | ~0.30 | 0.15 | 300 | B | 34.2 | 1.5 |
| XI | t-C$_8$H$_{17}$NH$_2$ | 0.350 | Primene 81-R | ~0.275 | 0.15 | 300 | B | 33.3 | 2.0 |
| XII | t-C$_8$H$_{17}$NH$_2$ | 0.425 | Primene 81-R | ~0.200 | 0.15 | 300 | B | 34.4 | 1.7 |
| XIII | t-C$_8$H$_{17}$NH$_2$ | 0.525 | Primene 81-R | ~0.10 | 0.15 | 300 | B | 33.6 | 1.8 |
| XIV | t-C$_8$H$_{17}$NH$_2$ | 0.30 | C$_6$H$_{11}$NH$_2$ | 0.325 | 0.15 | 300 | A | 29.1 | — |
| XV | t-C$_8$H$_{17}$NH$_2$ | 0.35 | C$_6$H$_{11}$NH$_2$ | 0.275 | 0.15 | 300 | A | 28.65 | 0.3 |
| XVI | t-C$_8$H$_{17}$NH$_2$ | 0.425 | C$_6$H$_{11}$NH$_2$ | 0.20 | 0.15 | 300 | A | 30.3 | 0.2 |
| XVII | t-C$_8$H$_{17}$NH$_2$ | 0.525 | C$_6$H$_{11}$NH$_2$ | 0.10 | 0.15 | 300 | A | 30.9 | 0.2 |
| XVIII | t-C$_8$H$_{17}$NH$_2$ | 0.30 | i-C$_3$H$_7$NH$_2$ | 0.325 | 0.15 | 250 | A | 16.5 | — |

| Example | % R—N=N—R | 10 Hr. t$\frac{1}{2}$ °C. | % R—N=N—R' | 10 Hr. t$\frac{1}{2}$ °C. | % R'—N=N—R' | 10 Hr. t$\frac{1}{2}$ °C. |
|---|---|---|---|---|---|---|
| I | 16.0 | ~160 | 48.2 | ~137 | 34.5 | ~107 |
| II | — | ~160 | 35.4 | ~137 | 63.1 | ~107 |
| III | 26.1 | ~160 | 54.1 | ~150 | 10.5 | ~160 |
| IV | — | ~160 | 60.5 | ~150 | 37.5 | ~160 |
| V | — | ~160 | 61.2 | ~150 | 32.5 | ~160 |
| VI | — | ~160 | 82.4 | ~150 | 14.0 | ~160 |
| VII | 16 | ~107 | 44 | ~137 | 26 | ~160 |
| VIII | 26 | ~107 | 47 | ~137 | 16 | ~160 |
| IX | 30 | ~107 | 46 | ~137 | 10 | ~160 |
| X | 32 | ~107 | 43 | ~137 | 12 | ~160 |
| XI | 34 | ~107 | 43 | ~137 | 11 | ~160 |
| XII | 43 | ~107 | 38 | ~137 | 6 | ~160 |
| XIII | 67 | ~107 | 22 | ~137 | 2 | ~160 |
| XIV | 20 | ~107 | 65 | ~140 | 121 | ~165 |
| XV | 32.6 | ~107 | 52.8 | ~140 | 99.2 | ~165 |
| XVI | 40.5 | ~107 | 47.5 | ~140 | 8.1 | ~165 |
| XVII | 47.2 | ~107 | 43.0 | ~140 | 6.5 | ~165 |
| XVIII | 32.6 | ~107 | 57.4 | ~135 | — | ~170 |

EXAMPLE XIX

Preparation of a Mixture of Di-tert-Amyldiazene, tert-Amyl tert-Butyldiazene, tert-Amyl tert-Octyldiazene, tert-Butyl tert-Octyldiazene and Di-tert-Octyldiazene The method of preparation of the sulfamide mixture was the same as that used for Table I except a mixture of three amines was employed. The mixture consisted of 0.22 mole tert-amylamine, 0.22 mole tert-butylamine and 0.22 mole of tert-octylamine. Upon working the reaction up according to the general procedure, a gas was purified by vacuum distillation. The pure amine distilled at 58° C. at 2 mm Hg.

The method of preparation of the sulfamide mixture was the same as that used for Table I except the reaction was run at ½ the scale and a mixture of 125 ml of hexane and 125 ml of methylene chloride was used as the solvent. The sulfuryl chloride (0.075 mole) was added to a solution of 0.187 mole tert-amylamine and 0.125 mole tert-cumylamine. The reaction was worked up according to the general procedure. Upon concentration of the sulfamide solution to approximately 125 mls, a large amount of white solids came out of solution. The solids were filtered off, washed with hexane and air dried on a watch glass. The filtrate was stripped to dryness and the residue was slurried in hexane and filtered. The filter cake was washed with hexane and dried with air. After drying the combined white solids weighed 16.6 grams and had a melting range of 95°–120° C. The solids were a mixture of N-tert-amyl-N'-tert-cumylsulfamide and N,N'-di-tert-cumylsulfamide. The hexane washings were stripped to dryness leaving 2.8 grams of a white solid. This was primarily N,N'-di-tert-amylsulfamide.

All the white solids were combined, slurried in 50 mls of hexane and oxidized with a solution of 0.5 grams of Adogen 464 product and 17.5 grams of 50% sodium hydroxide in 125 grams of 14.2% bleach according to General Method B. Upon completion of the reaction and workup, a tan semi-solid weighing 14.4 grams was obtained.

The semi-solid was slurried in 15 mls of cold pentane and filtered. The filter cake was rinsed with 5 mls of cold pentane and air dried. The dried filter cake weighed 3.6 grams and had a melting range of 112°–114° C. It was identified by its melting point and infrared spectrum as 2,3-dimethyl-2,3-diphenylbutane, the major decomposition product of azocumene. Azocumene was the expected oxidation product of the N,N'-di-tert-cumylsulfamide in the sulfamide mixture but azocumene decomposes thermally above 45° C. and the reaction was run around 65° C.

The pentane filtrate was stripped on a rotary evaporator under reduced pressure leaving a light brown liquid weighing 8.15 grams. Gas chromatographic analysis indicated the liquid consisted of 14.5% di-tert-amyldiazene, 68.2% tert-amyl tert-cumyldiazene and 11.5% residual 2,3-dimethyl-2,3-diphenylbutane.

EXAMPLE XXI

Preparation of tert-Butyl tert-Cumyldiazene

The method of preparation of the sulfamide mixture was the same as that employed in Example XX except 0.187 mole of tert-butylamine was substituted for the tert-amylamine. The solvent was stripped off and the solid sulfamide mixture was slurried in 75 ml of hexane and oxidized by General Method B with a solution of 17.5 grams of 50% sodium hydroxide and 0.5 grams of Adogen 464 product in 125 grams of 14.2% bleach. Upon completion of the reaction and workup, a white solid weighing 12.1 grams was obtained.

The residue was slurried in 20 mls of cold pentane and filtered. The filter cake was air dried and weighed 4.3 grams. A gas chromatographic scan of a small amount of the solid in hexane indicated it was approximately 22% of tert-butyl tert-cumyldiazene and 76% of 2,3-dimethyl-2,3-diphenylbutane, the major decomposition product of azocumene.

The filtrate was stripped of pentane on the rotary evaporator. The residue weighed 7.0 grams. A gas chromatographic scan indicated that it consisted of 65% of tert-butyl tert-cumyldiazene and 23% of 2,3-dimethyl-2,3-diphenylbutane.

EXAMPLE XXII

Preparation of a Mixture of Dodecyl, Tridecyl, and Tetradecyl Diazenes

The method of preparation of the sulfamide mixture was the same as that used for Table I except 130 grams (approximately 0.65 mole) of Primene 81-R product was used. No other amine was employed. Upon the addition of water, a clear hexane solution of the sulfamides was obtained. The hexane solution was washed with a 10% HCl aqueous solution to remove the excess Primene 81-R product and the hydrochlorides. The hexane solution was washed with saturated sodium bicarbonate solution, dried over sodium sulfate, filtered, and heated to stripped off the hexane. The residue was a viscous straw yellow liquid weighing 73.8 grams.

The crude sulfamide was dissolved in 100 mls of hexane and transferred to a 1 liter 3-neck flask. It was oxidized with a solution of 60 grams of 50% NaOH in 500 grams of 13.9% bleach according to Method A. After distillation of most of the hexane, the reaction mixture was stirred an additional three hours at 80°–85° C. The reaction mixture was cooled to 50° C. and the hexane that distilled off was added back; the reaction mixture then was transferred to a separatory funnel. The aqueous layer was separated and the hexane layer was worked up according to the general procedure. After stripping off the hexane, the yellow liquid residue weighed 29.3 grams.

The crude azo was diluted with 100 mls of hexane and cooled to 10° C. in an ice water bath; then 50 ml of 77% $H_2SO_4$ was added slowly with rapid stirring to the cooled azo solution. The acid layer turned burgundy red.

The mixture was stirred 5 minutes and transferred to a separatory funnel. The lower red acid layer was drained onto 100 grams of ice and the mixture was diluted with 500 ml water. Upon stirring, the red color slowly disappeared and a yellow organic layer formed. The yellow organic layer was taken up in 100 ml of hexane and the mixture was transferred to a separatory funnel. The acid layer was separated and the hexane layer was washed successively with water and saturated sodium bicarbonate. The hexane solution was dried over sodium sulfate, filtered, and heated on a rotary evaporator under reduced pressure to strip off the hexane. The residue was a yellow liquid weighing 21.1 grams. The residue was a mixture of several azo compounds which could not be separated completely by gas or liquid chromatography. This mixture consisted of di-tert-dodecyldiazene, di-tert-tridecyldiazene, di-tert-tetradecyldizene, tert-dodecyl tert-tridecyldiazene, tert-dodecyl tert-tetradecylidiazene, and tert-tridecyl tert-tetradecyldiazene.

EXAMPLE XXIII

Curing an Unsaturated Polyester-Styrene Resin with a Mixture of Di-tert-Octyldiazene, tert-Octyl tert-Dodecyldiazene, and Di-tert-Dodecyldiazene An unsaturated polyester resin was prepared by reacting maleic anhydride (1.0 mole), phthalic anhydride (1.0 mole), and propylene glycol (2.2 moles) until an acid number of 45–50 was obtained. To this was added hydroquinone at a 0.013% concentration. Seven parts of the unsaturated polyester were diluted with 3 parts of monomeric styrene to obtain a homogeneous blend having a viscosity of 13.08 poise and a specific gravity of 1.14.

To 20 grams of this blend was added 0.28 gram of a mixture of approximately 67% of di-tert-octyldiazene, 22% of tert-octyl tert-dodecyldiazene, and 2% of di-tert-dodecyldiazene; the mixture was stirred well with a wooden spatula. The sample was poured into a test tube and the test tube was placed in a 121° C. oil bath. The internal temperature was recorded as a function of time and a peak exotherm of 228° C. was reached in 6.4 minutes indicating that an excellent cure of the unsaturated polyester-styrene resin blend had occurred.

Without an initiator, no cure of the resin blend occurred even after 30 minutes.

EXAMPLE XXIV

Curing an Unsaturated Polyester-Styrene Resin With a Mixture of Di-tert-Octyldiazene, tert-Octyl Cyclohexyldiazene and Di-Cyclohexydiazene The procedure of Example XXIII was repeated using 0.28 gram of a mixture of approximately 24% of di-tert-octyldiazene, 60% of tert-octyl cyclohexyldiazene, and 14% of di-cyclohexyldiazene and 20 grams of the polyester-styrene blend. The sample was poured into a test tube; the test tube was placed in a 121° C. oil bath. The internal temperature was recorded as a function of time reaching a peak exotherm of 203° C. in 6.6 minutes which indicated that an excellent cure of the unsaturated polyester-styrene resin blend had occurred.

EXAMPLE XXV

Polymerization of Styrene with a Mixture of Di-tert-Octyldiazene, tert-Dodecyl tert-Octyldiazene, and Di-tert-Dodecyldiazene A solution of 0.00875 gram of the mixed diazene solution from Example XII in 35 grams of sytrene was prepared in a clean dry 2 oz. glass bottle with a polypropylene liner on the cap. Five ml of the solution were transferred to each of five 16×150 mm pyrex test tubes. The tubes were partially submerged in an ice bath and flushed with nitrogen for 30 seconds. The test tubes were then sealed with a natural gas-oxygen flame. The test tubes were then stored at −18° F. until ready to use.

The test tubes were taken out of the freezer and allowed to warm up to room temperature for 15 minutes. They were then placed in a constant temperature oil bath preheated to 116° C. The tubes were heated in the oil bath for 1.5 hours, the temperature raised to 132° C. for 1.5 hours, the temperature raised again to 149° C. for another 1.5 hours and finally the temperature raised to 160° C. for the final 1.5 hours. There was a lag time of around five minutes until the bath temperature reached the next temperature in the profile. This was included in the 1.5 hour reaction time at that temperature. Test tubes were withdrawn after 0.75, 1.5, 3.0, 4.5, and 6.0 hours.

The test tubes were rinsed in acetone to cool and clean them. The tubes were cut open with a tone wheel and the contents dissolved in toluene-quinone solutions in 150 ml beakers. The solutions were allowed to stand overnight and then stirred one hour on a magnetic stirrer. The polymer was then precipitated by dropwise addition of the soltuion to vigorously stirred methanol. The polymer was filtered off and dried in a vacuum oven overnight. The next day the weight of the polymer was determined for each of the five samples and a time versus % conversion table was prepared. The results are summarized in Table II.

The viscosity average molecular weight ($\overline{M}_v$) was determined on the 4.5 hour and 6.0 hour samples. Into a 25 ml volumetric flask was weighed 0.500 gram of polymer. Approximately 20 ml of toluene were added to dissolve the polymer. The flask and contents were warmed to 25° C. and the dilution to 25 ml was completed with 25° C. toluene. The solution was filtered and 10 ml of the filtrate were pipetted into a Cannon-Ubelhode no. 75 viscometer in a 25° C. water bath. Three flowtimes through the viscometer were determined. The solution was diluted with 5 ml more of 25° C. toluene and mixed; three more flowtimes were determined. Two more 5 ml dilutions were carried out and the flowtimes were determined. The intrinisic viscosity [$\eta$] was determined from the concentration of the solutions and the relative viscosities of the solutions. $\overline{M}_v$ was then calculated from the Mark-Houwink equation where

[$\eta$]=$K'\overline{M}_v^a$ where ($K'$) and ($a$) are constants for a given polymer type, solvent, and temperature.

$\overline{M}_w, \overline{M}_n$, and $\overline{M}_z$ were determined by analysis of GPC scans.

Similar polymerizations were carried out thermally and with three high temperature peroxides for the sake of comparison (See Table III). The polymer prepared from the mixed diazenes had the narrowest molecular weight distribution.

TABLE II

Styrene Bulk Polymerization
Initiator: 0.025 PHM
Mixed Diazenes from Example XII

| Time (Hrs.) | Temp. °C. | % Conversion | $\overline{M}_v \times 10^{-3}$ | Thermal Polym. % Conversion | $\overline{M}_v \times 10^{-3}$ |
|---|---|---|---|---|---|
| 0.75 | 116 | 9 | 309 | 11 | 299 |
| 1.50 | 116 | 15 | 323 | 18 | 312 |
| 3.00 | 132 | 43 | 278 | 55 | 276 |
| 4.50 | 149 | 82 | 247 | 94 | 230 |
| 6.00 | 160 | 92 | 227 | 100 | 222 |

TABLE III

Styrene Bulk Polymerization
The Effect of Various Initiators on the Molecular Weight Distribution of Polystyrene
Initiator = 0.025 phm Pure Basis

| Initiator | % Conversion | $\overline{M}_v \times 10^{-3}$ | $\overline{M}_w \times 10^{-3}$ | $\overline{M}_n \times 10^{-3}$ | $\overline{M}_z \times 10^{-3}$ | $\overline{M}_w/\overline{M}_n$ | $\overline{M}_z/\overline{M}_n$ |
|---|---|---|---|---|---|---|---|
| Mixed Diazenes (Example XII) 4.5 hour sample | 94 | 230 | 323 | 171 | 505 | 1.89 | 2.95 |
| Mixed Diazenes (Example XII) 6.0 hour sample | 100 | 222 | 331 | 162 | 487 | 1.92 | 3.01 |
| Thermal | 92 | 227 | 308 | 146 | 497 | 2.11 | 3.40 |
| 1,1-Di(tert-butylperoxy) cyclohexane (80% in butyl benzyl phthalate) | 96 | 241 | 313 | 148 | 501 | 2.11 | 3.39 |
| 1,1-Di(tert-buylperoxy)-3,3,5-trimethylcyclohexane | 92 | 257 | 329 | 151 | 524 | 2.18 | 3.47 |
| Ethyl 3,3-di(tert-buylperoxy) butyrate (75% in Odorless | 96 | 212 | 278 | 126 | 442 | 2.21 | 3.51 |

TABLE III-continued

Styrene Bulk Polymerization
The Effect of Various Initiators on the Molecular Weight Distribution of Polystyrene
Initiator = 0.025 phm Pure Basis

| Initiator | % Conversion | $\overline{M}_v \times 10^{-3}$ | $\overline{M}_w \times 10^{-3}$ | $\overline{M}_n \times 10^{-3}$ | $\overline{M}_z \times 10^{-3}$ | $\overline{M}_w/\overline{M}_n$ | $\overline{M}_z/\overline{M}_n$ |
|---|---|---|---|---|---|---|---|
| mineral spirits) | | | | | | | |

What is claimed:

1. A process of preparing a mixture of azoalkanes comprising reacting 4 equivalents of a mixture of at least two amines having the structures R'—NH$_2$ and R—NH$_2$ wherein R and R' are different and independently selected from the group consisting of a straight chain or branched alkyl of 1 to 22 carbons, a cycloalkyl of 3 to 12 carbons, and an aralkyl of 7 to 11 carbons, with the proviso that there can not be two aralkyl groups on the same azoalkane, with 1 equivalent of sulfuryl chloride in an anhydrous inert solvent until the reaction is completed, and then oxidizing the mixture of sulfamide products with basic bleach after removing the amine hydrochloride side products with an aqueous wash to form the mixture product of at least two azoalkanes, at least one of which is unsymmetrical of the structure R—N=N—R' and at least one other is symmetrical of the structure R'—N=N—R' or R—N=N—R', with the further proviso that in the oxidation of the more difficult to oxidize sulfamides, the solvent content is reduced to a minimal amount prior to the addition of the oxidizing solution or during the oxidation reaction.

2. The process of claim 1 where the azoalkane mixture contains di-tert-octyldiazene, tert-octyl tert-dodecyldiazene, and di-tert-dodecyldiazene and the starting amines are tert-octylamine and a commercial mixture of tert-alkyl primary amines in the C$_{12}$–C$_{14}$ range.

3. The process of claim 1 where the azoalkane mixture contains di-tert-octyldiazene and cyclohexyl tert-octyldiazene and the starting amines are tert-octylamine and cyclohexylamine.

4. The process of claim 1 where the azoalkane mixture contains di-tert-octyldiazene and tert-amyl tert-octyldiazene and the starting amines are tert-octylamine and tert-amylamine.

5. The process of claim 1 where the azoalkane mixture contains di-tert-octyldiazene and tert-butyl tert-octyldiazene and the starting amines are tert-octylamine and tert-butylamine.

6. The process of claim 1 wherein the azoalkane mixture contains di-tert-dodecyldiazene, di-tert-tridecyldiazene, di-tert-tetradecyldiazene, tert-dodecyl tert-tridecyldiazene, tert-dodecyl tert-tetradecyldiazene, and tert-tridecyl tert-tetradecyldiazene and the starting amines are the commercial mixture of tert-alkyl primary amines where the alkyl groups have 12–14 carbons.

7. The process of claim 1 wherein the oxidation reaction is carried out in a temperature range of 65° C. to 90° C. and is completed in ½ to 3 hours.

8. The process of claim 7 wherein the mixture product has at least one unsymmetrical azoalkane of the structure R—N=N—R', at least one symmetrical azoalkane of the structure R—N=N—R, and at least one symmetrical azoalkane of the structure R'—N=N—R'.

* * * * *